(12) United States Patent
Shalaby

(10) Patent No.: US 6,780,799 B2
(45) Date of Patent: Aug. 24, 2004

(54) ANTIMICROBIAL FABRICS

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 10/453,804

(22) Filed: Jun. 3, 2003

(65) Prior Publication Data

US 2003/0211794 A1 Nov. 13, 2003

Related U.S. Application Data

(62) Division of application No. 09/506,046, filed on Feb. 17, 2000, now Pat. No. 6,596,657.
(60) Provisional application No. 60/120,392, filed on Feb. 17, 1999.

(51) Int. Cl.[7] .................. B32B 27/04; B32B 27/12; B32B 27/20; B32B 5/02
(52) U.S. Cl. ................ 442/123; 442/59; 442/164; 442/171; 442/327; 524/582; 524/583
(58) Field of Search ................ 442/320, 326, 442/268, 270, 271, 327, 59, 123, 164, 171; 524/582, 583

(56) References Cited

U.S. PATENT DOCUMENTS

| | | | |
|---|---|---|---|
| 2,803,584 A | | 8/1957 | Hodge et al. ............... 167/65 |
| 3,629,477 A | | 12/1971 | Model et al. ............... 424/340 |
| 5,091,102 A | * | 2/1992 | Sheridan ................ 15/104.93 |
| 5,491,198 A | | 2/1996 | Shalaby et al. ............ 525/340 |
| 5,707,736 A | * | 1/1998 | Levy et al. ................ 428/375 |
| 6,069,192 A | * | 5/2000 | Shalaby et al. ............ 523/205 |

OTHER PUBLICATIONS

Arthur, Jr., J.C., Chap. 38, pp. 574–591, *Addition & Condensation Polymerization Processes*, vol. 91, Advances in Chemistry Series, Amer. Chem. Soc., Washington, DC (1969).

Shalaby, S.W., et al., *Copolymerization of Caprolactam with Polyoxybutylene Diamine*, J. Polym. Eng. & Sci., 13, 88 (1973).

Corbett, J.T., et al., *In Vitro and In Vivo Release of Vancomycin and Gentamicin from an Injectable Absorbable Gel-forming Matrix for Treating Osteomyelitis*, presented to the Materials Research Society, 351, 1977.

* cited by examiner

Primary Examiner—Elizabeth M. Cole
Assistant Examiner—Norca L. Torres
(74) Attorney, Agent, or Firm—Leigh P. Gregory

(57) ABSTRACT

The present invention is directed to surface functionalized fabrics, particularly those based on non-woven polypropylene, wherein the functional groups are capable of binding antimicrobial agents through ionic conjugation to control their release and prolong their antimicrobial activity. The invention also deals with Nylon 6 fabric that is complexed with iodine to control its release and to achieve prolonged antimicrobial activities. Similarly, polypropylene and cellulosic fabrics grafted with N-vinylpyrrolidone are disclosed. The N-vinylpyrrolidone can also complex with iodine to control its release and provide antimicrobial activity over desired periods of time.

6 Claims, No Drawings

ANTIMICROBIAL FABRICS

This is a divisional application of U.S. Ser. No. 09/506,046, filed Feb. 17, 2000 now U.S. Pat. No. 6,596,657, which claims the benefit of prior provisional application, U.S. Serial No. 60/120,392, filed Feb. 17, 1999.

BACKGROUND OF THE INVENTION

Natural and synthetic fabrics and particularly synthetic, non-woven fabrics have been used extensively in the production of light-weight components for healthcare and sportswear products as well as components for transportation vehicles, including airplanes and spacecraft. Rendering fabrics, in general, and particularly non-woven ones, antibacterial, using conventional and novel processes, has been called for by textile manufacturers and users. These circumstances and recent developments of the surface phosphonylation technology or permanent attachment of reactive phosphonate groups on synthetic polymers and established ability of iodine to form an antimicrobial agent when complexed with polyvinylpyrrolidone provided an incentive to look for novel approaches to produce new fibrous substrates that display antimicrobial (or antibacterial) activities, preferably over prolonged periods of time through modulating the release of the antimicrobial (or antibacterial) agents.

SUMMARY OF THE INVENTION

DETAILED DESCRIPTION OF PREFERRED EMBODIMENTS

In one aspect of the present invention is concerned with introducing and controlling the release of known and novel forms of broad-spectrum antibacterial agents in unmodified or surface-phosphonylated fabrics and particularly non-woven polypropylene fabrics (NPPF) and non-woven Nylon 6 fabrics (NNF). More generally, the present invention is concerned with rendering a variety of non-woven and woven fabrics and knitted fabrics, including those made of polyethylene, polyesters, nylons, and acrylic copolymers, antimicrobial.

Surface phosphonylation of polymeric substrates is disclosed in U.S. Pat. No. 5,491,198 to Shalaby, et al., which is hereby incorporated herein by reference. In accordance with the present invention, it has been discovered that both unmodified and surface-phosphonylated fabrics can be treated with antimicrobial agents in a manner which allows for the incorporation of controlled release of those agents. Thus, with surface phosphonylated fibers, ionic conjugation of antimicrobial agents to the functionalized surfaces (following the appropriate post-treatment to create anionic or cationic binding sites to cationic and anionic agents, respectively) allows for incorporating and controlling the release of the antimicrobial agents and imparting antimicrobial activity over prolonged periods during fabric end-use.

In another aspect of this invention, non-modified fiber surfaces (such as those of polypropylene, polyethylene, and similar fibers used in the textile industry) containing antimicrobial agents such as triclosan (which has a high propensity to sublime or evaporate from the fibers when used as a surface auxiliary) is used in a practically non-volatile salt under usual end-use conditions. It is also the object of this invention to provide a method for introducing the triclosan salt, as well as similar agents, into the subsurface of the fiber to control its release and allow for prolonged antimicrobial activities.

In another aspect of this invention, the demonstrated ability to complex iodine with polyvinylpyrrolidone in solution to produce an effective antimicrobial liquid was extended to develop novel solid polymeric substrates displaying antimicrobial activities. More specifically, these solid substrates are fibers made of polyamides, such as nylon or polymers other than polyamides, but grafted with amide-bearing chains. These grafted polymers are capable of complexing with iodine to modulate its release and hence, produce fibers with prolonged antimicrobial activity. More specifically, the polyamide fibers comprise Nylon 6 and the grafted fibers comprise polypropylene, polyethylene, polyester, and cellulosic fibers.

Of the many available antibacterial agents, those discussed below were selected to (1) be active against both gram-positive and gram-negative bacteria; (2) provide a diverse mode of action; (3) explore novel forms for modulating their release; and (4) allow the use of the most suitable agents for NPPF or NNF.

Chlorhexidine (CXD)—Chlorhexidine is available as a salt of gluconic, acetic acid, or hydrochloric acid. The free base is a bis-guanidine with strong bacteriostatic activity [Davies, G. e., *Brit. J Pharmacol.*, 9, 192 (1954)]. It is very basic and forms salts with most acids quite readily. It is sparingly soluble in water. However the diacetate is soluble in water and alcohol. The aqueous solution decomposes when heated to above 70° C. The salts of CXD are used as an antiseptic or disinfectant. It is well established, clinically, that CXD gluconate provides antimicrobial effects against a wide range of microorganisms including gram-positive and gram-negative bacteria. It is indicated for surgical scrub, skin wound cleanser, and pre-operative showering.

Benzalkonium Chloride (BAC)—This is a mixture of alkyldimethylbenzylammonium chlorides (the alkyl groups consisting of $C_8H_{17}$ to $C_{18}H_{37}$ groups) with established antimicrobial activity [Gump, W., in KIRK-OTHMER *Encyclopedia of Chemical Technology*, Vol. 7, Wiley, 3$^{rd}$ Ed., 1979, p. 815]. It is a cationic surface active agent, available as an amorphous powder that is soluble in water and alcohol. It is a rapidly acting anti-infective agent with moderately long duration of action. BAC is active against bacteria, fungi, protozoa, and some viruses. Solutions of BAC are bacteriostatic or bactericidal according to their concentrations. BAC complexes combine readily with anionic detergents.

Mupirocin (Pseudomonic Acid A)—Mupirocin, a topical antibacterial, is produced by fermentation of the organism *Pseudomonas fluorescans* [Chain, B. and Mellows, G., *Chem. Commun.*, 847 (1974); Fuller, A. T. et al, *Nature*, 234, 216 (1971)]. The total synthesis of the (±)-form was reported by Snider and coworkers [*J. Org. Chem.*, 48, 303 (1983)]. Mupirocin is soluble in alcohol. It inhibits bacterial protein synthesis by reversibly and specifically binding to bacterial isoleucyl transfer-RNA synthetase. Hence, mupirocin shows no cross-resistance with gentamicin and tetracycline (Casewell, M. W. and Hill, R. L. A., *Antimicrob. Chemother.*, 19, 1 (1987); Ward, A. and Campoli-Richards, D. M., *Drugs*, 32, 425 (1986)]. The following gram-positive bacteria are susceptible to mupirocin in vitro [Casewell, M. W. and Hill, R. L. A., *Antimicrob. Chemother.*, 19, 1 (1987); *Antimicrob. Chemother.*, 15, 523 (1985)] *S. aureus, S. epidermidis* and *S. pyogenes*. Clinically, it is indicated for the treatment of impetigo due to *S. aureus* and *S. pyogenes*.

Zinc Salts and Complexes—A number of zinc salts and complexes have been noted to have antiseptic or antibacterial activities. Zinc acetate is used in veterinary medicine as an antiseptic agent [Budavari, S. (Ed.), *The Merck Index*, 20th Ed., Merck & Co., Inc., Whitehouse Station, N.J., 1996]. An aqueous solution of zinc sulfate is used as a mild astringent for temporary relief of minor eye irritation. Zinc propionate is used on adhesive tape plaster for irritation caused by fungi and bacterial action. It is also used topically as an antifungal agent [Budavari, S. (Ed.), *The Merck Index*, 20th Ed., Merck & Co., Inc., Whitehouse Station, N.J., 1996]. Bacitracin zinc complex (prepared by the action of zinc salts on bacitracin broth) is a water-soluble powder that contains about 7 percent zinc and is used as an antibacterial agent (Hodge, L., U.S. patent (to CSC) U.S. Pat. No. 2,803,584 (1957)].

Triclosan (TSN)—This is a phenolic compound derived from chlorinated phenyl oxide. It is a crystalline compound that is insoluble in water, but readily soluble in alkaline solutions and organic solvents. It is used as a bacteriostat and preservative for cosmetic and detergent preparations (Model, E. and Bindler, J., U.S. patent (to Geigy) U.S. Pat. No. 3,629,477 (1971); Savage, C. A., *Drug. Cosmet. Ind*, 109(3), 36,161 (1971)]. Over the past few years, TSN has been recognized by the film and textile industry as a highly effective bacteriostatic agent against a wide range of gram-positive and gram-negative bacteria.

Complexes of Polyamides with Iodine—The most common complex of iodine with polyamide is that containing polyvinyl pyrrolidone (or povidone). The complex is known as povidone-iodine (Shelanski, S. J., *Int. Coll. Surgeons*, 25, 727 (1956)]. It is water soluble and contains 9 to 12 percent available iodine. It retains iodine's bactericidal activity, but less potently. The complex is also soluble in alcohol. It is has been applied in several formulations as a topical anti-infective agent, including those used as surgical scrub. Iodine preparations, in general, are of common use for their broad microbicidal spectrum against bacteria, fungi, viruses, spores, protozoa, and yeasts.

The invention may be further understood by reference to the following examples, which are provided for the purpose of representation, and are not to be construed as limiting the scope of the invention.

EXAMPLE 1

Surface-Phosphonylation and Characterization of Non-Woven Polypropylene Fabric (NPPF)

The phosphonylation of the low-density NPPF is conducted following the gas phase process described in U.S. Pat. No. 5,491,198, using phosphorous trichloride and oxygen under dry conditions. The phosphonylation times of 2 and 15 minutes are used depending on the fabric bulk density. Removal of trace amounts of $PCl_3$ is achieved using a dry, non-reactive solvent. The fabrics are analyzed by SEM/EDX (using a scanning electron microscope with an electron dispersive X-ray attachment) for percent P and elemental analysis for percent P and Cl. The tensile properties of the fabric are measured using an MTS 858 Minibionix Universal Tester. Following phosphonylation, the fabric is stored in a dry environment for no more than several hours prior to subsequent treatments.

EXAMPLE 2

Hydrolysis of Phosphonylated NPFF

A batch hydrolysis reaction is conducted to convert the $—P(O)Cl_2$ group of the phosphonylated fabrics to $—P(O)(OH)_2$ groups. The extent of the hydrolysis is monitored by elemental analysis for percent chlorine; the concentration of acid groups is determined by acidimetry. At this point, the treated fabrics are then tested to determine any changes in tensile properties using an MTS 858 Minibionix Universal Tester in the tensile mode.

EXAMPLE 3

Reaction of Phosphonylated NPPF with Hexanediamine

This reaction is conducted on the virgin phosphonylated surface using a hexanediamine solution in a suitable non-reactive solvent, preferably chloroform, at room temperature. Excess diamine is removed by rinsing with pure solvent. The fabric is dried and then analyzed for extent of reaction by elemental analysis for percent nitrogen. The basicity of the surface is determined by titration. The tensile properties of the fabrics are then evaluated using the MTS-858 Minibionix Universal Tester.

EXAMPLE 4

Ionic Binding (or Conjugation) of Chlorhexidine to Phosphonic Acid-Bearing NPPF

For preparing an ionic conjugate of NPPF carrying a $—P(O)(OH)_2$ group, the fabric prepared according to Example 2 is used. Thus, the treated NPF is incubated with a concentrated solution (5–15 percent) of chlorhexidine acetate in ethanol at room temperature for different periods of time. At the conclusion of the incubation period, the fabrics are removed, rinsed with cold ethanol, and air dried. The extent of binding, depending on the reaction conditions, are determined by elemental analysis for percent nitrogen. The tensile properties of the fabric are determined using the MTS-858 Minibionix Universal Tester.

EXAMPLE 5

Ionic Binding (or Conjugation) of Benzalkonium Chloride (BAC) to Phosphonic Acid-Bearing NPPF Binding of benzalkonium chloride is conducted in a similar manner to that described for reacting chlorhexidine acetate in Example 4. However, depending on the up-take of BAC from its ethanol solution, BAC is alternatively applied as a water solution. Characterization of the conjugated fabrics is conducted as in Example 4.

EXAMPLE 6

Ionic Binding (or Conjugation) of Mupirocin to Amine-Bearing NPPF

To bind the acidic mupirocin, the amine-bearing NPPF, prepared according to the procedure of Example 3, is used. The ionic binding procedure is similar to that used for binding chlorhexidine acetate in Example 4. For this, a solution of mupirocin in ethanol is used. The content of bound mupirocin is determined by elemental analysis for percent nitrogen. The tensile properties of the fabrics is measured using the MTS-858 Minibionix Universal Tester.

EXAMPLE 7

Binding Zinc Ions to Phosphonic Acid-Bearing NPP

Binding of zinc ions to NPPF requires the use of zinc acetate solution in ethanol or water (depending on the desired up-take) and the phosphonic acid-bearing NPPF prepared according to the procedure described in Example 2. The binding process is similar to that used in binding chlorhexidine acetate in Example 4. Depending on the up-take of zinc acetate from the solution, incubation of the fabrics is conducted using a zinc acetate solution in water or alcohol. The extent of binding is determined by elemental analysis for zinc. Atomic absorption is used to determine the zinc content in the fabrics. The tensile properties of the fabrics are measured using the MTS-858 Minibionix Universal Tester.

EXAMPLE 8

Preparation of Triclosan Sodium (TCS-Na)

The TCS-Na (a phenate salt) is prepared by reacting triclosan with sodium methoxide in methanol. A solution of triclosan in 2-propanol is treated with a stoichiometric amount of sodium methoxide at 0–10° C. The solid salt is isolated by evaporating the organic solvent under reduced pressure in the absence of moisture. The salt is analyzed to confirm its identity using infrared spectroscopy and elemental analysis for sodium, carbon, and chlorine. The thermal properties of the phenate salt are determined by differential scanning calorimetry (DSC) and thermogravimetric analysis (TGA).

EXAMPLE 9

Incorporation of TCS-Na in NPPF

This is conducted by incubating the fabrics in an aqueous 2-propanol solution at variable temperatures for different periods of time. At the conclusion of the incubation period, the fabric is removed, rinsed with cold water, and air dried. The TCS-Na content in the fabrics is determined by elemental analysis for percent sodium and chlorine. Atomic absorption spectroscopy is used to determine the sodium content. The thermal and tensile properties of the NPPF containing TCS-Na are determined using TGA and the MTS 858 Minibionix Universal Tester, respectively.

EXAMPLE 10

Incorporation of TCS-Na in Non-Woven Nylon 6 Fabric (NNF)

This is accomplished as described in Example 9 for the NPPF case. The resulting fabric is characterized/tested as described in Example 9.

EXAMPLE 11

Preparation of Oligomeric Nylon 6 (O-N6)

Low molecular weight (oligomeric) Nylon 6, having a degree of polymerization of about 10, is prepared by hydrolytic polymerization (in the presence of water) of ε-caprolactam using a predetermined amount of hexanediamine, as initiator/chain control agent. The reaction is conducted at about 230° C. following a similar reaction scheme to that used earlier by Shalaby and coworkers [Shalaby, S. W. et al., Copolymerization of Caprolactam with Polyoxybutylene Diamine, *J. Polym. Eng. Sci.*, 13, 88 (1973)]. The resulting polymer is extracted with cold water to remove unreacted caprolactam. The dry polymer is characterized by DSC for its $T_m$, and also solution viscosity and end-group analysis.

EXAMPLE 12

Preparation of NPPF Grafted with N-Vinyl Pyrrolidone (NPPF-PVP)

The grafting experiments are conducted in an aqueous medium following typical redox, free radical polymerization and using a combination of ferrous sulfate and hydrogen peroxide. A process similar to that reported by Arthur [Arthur, Jr., J. C., Chap. 38 in *Addition & Condensation Polymerization Processes*, (J. A. J. Platzer, Ed.), Vol. 91, Advances in Chemistry Series, Amer. Chem. Soc., Washington, D.C., (1969)] is used. The unreacted monomer and free polyvinyl pyrrolidone remain in the aqueous medium after removal of the grafted fabric which is then rinsed with water. The extent of grafting is determined by elemental analysis for percent nitrogen.

EXAMPLE 13

Iodine-Complex with Oligomeric Nylon 6 (O-N6/$I_2$)

This is achieved by two methods. The first method entails incubating the O-N6 microparticles (prepared by jet-milling a ground O-N6 to produce particles having an average diameter of 5:) in an ethanol solution of $I_2$ at different temperatures for different periods of time. The resulting O-N6/$I_2$ is isolated by filtration. The second method consists of dissolving the nylon microparticulates in hot ethylene glycol. This is then cooled to a minimum temperature without causing the O-N6 to precipitate. At this point, iodine is introduced and the reaction mixture is maintained at that temperature for different periods of time. The O-N6/$I_2$ complex is allowed to precipitate by cooling. The thermal properties of the O-N6/$I_2$ complex are determined by DSC and TGA.

EXAMPLE 14

Formation of Iodine Complex with Non-Woven Nylon 6 Fabric (NNF) to Form NNF/$I_2$ Method A—NNF is treated in the same manner as the O-N6 solid microparticulates described in the first method of Example 13.

Method B—NNF is immersed (or padded) in a solution of 12 in ethylene glycol.

Method C—NNF is immersed (or padded) in a solution of O-N6/$I_2$ complex in a moderately heated ethylene glycol as described in the second method of Example 13.

The fabric resulting from any of these methods is kept in contact with the 12 solution for different periods of time. The treated fabric is then removed, rinsed with water, and air dried. The thermal properties of the fabric are determined by DSC and TGA. The tensile properties of the fabric are determined using the MTS Universal Tester.

EXAMPLE 15

Preparation of Iodine Complex with NPPF-PVP (NPPF-PVP/$I_2$)

The NPPF having polyvinyl pyrrolidone grafts (i.e., NPPF-PVP) are prepared as described in Example 12. The NPPF-PVP is then immersed (or padded) for different periods of time with an ethanol solution of 12 at different temperatures. At the conclusion of the incubation period, the NPPF-PVP/$I_2$ is removed, rinsed with cold ethanol, and air dried. The thermal properties of the fabric are determined using DSC and TGA. The tensile properties of the fabric are determined using the MTS 858 Minibionix Universal Tester.

EXAMPLE 16

Preparation of Woven Cotton Fabric (WCF) Grafted with N-vinylpyrrolidone (WCF-VP)

The grafting experiment is conducted in an aqueous medium following typical redox, free radical polymerization and using a combination of ferrous sulfate and hydrogen peroxide. A process similar to that reported by Arthur [Arthur, Jr., J. C., Chap. 38 in *Addition & Condensation Polymerization Processes*, (J. A. J. Platzer, Ed.), Vol. 91, Advances in Chemistry Series, Amer. Chem. Soc., Washington, D.C., (1969)] is used. The unreacted monomer and free polyvinyl pyrrolidone remain in the aqueous medium after removal of the grafted fabric. The grafted fabric is then rinsed with water. The extent of grafting is determined by elemental analysis for percent nitrogen.

EXAMPLE 17

Preparation of Iodine Complex with WCF-PVP (WCF-PVP/$I_2$)

The WCF having polyvinylpyrrolidone grafts (i.e., WCF-PVP) are prepared as described in Example 16. The WCF-PVP is then immersed (or padded) for different periods of time with an ethanol solution of $I_2$ at different temperatures. At the conclusion of the incubation period, the WCF-PVP is removed, rinsed with ethanol, and air dried. The thermal properties of the fabric are determined using DSC and TGA. The tensile properties of the fabric are determined using the MTS 858 Minibionix Universal Tester.

EXAMPLE 18

Controlled Release of the Active Agents from Treated NPPF and NNF

The release studies of all the organic antibacterial agents are conducted using a batch and continuous-flow processes. In the batch process, the fabrics are exposed to isotonic saline solution and temperatures between 25° C. and 40° C. Samples of the saline solution are analyzed daily for a period of one week for the amount of released agent, using reversed-phase high-performance liquid chromatography (HPLC). For the HPLC analysis, an experimental protocol and standard curve are developed for each of the active agents. Meanwhile, the continuous release study is conducted in a continuous-flow system at 37° C. using saline solution at a flow rate of about 50:1/hr. Samples are collected every two days over a period of two weeks and concentration of the released active agent is determined by HPLC.

For the release of zinc-treated fabrics, both the batch and continuous process, are pursued as described above. However, the concentration of the released zinc ions is determined using atomic absorption spectroscopy. For fabrics comprising an iodine complex, the analysis of released $I_2$ is conducted only using the batch process. The amount of released $I_2$ is determined using iodometry.

EXAMPLE 19

Evaluation of the Antibacterial (or Antimicrobial) Properties of Treated NPPF and NNF The antibacterial activities of different fabrics (which are pre-washed once, twice, or five times with water at 40° C.) are pursued using (1) *E. coli* as a typical gram-negative bacteria and *S. epidermidis* as a gram-positive bacteria; (2) the parallel streak method (AATTC-147) first for qualitative assessment, followed by the AATTC-100 method for quantitative evaluation; (3) gentamicin as a positive control antibacterial agent for *E. coli* cultures without the fabric-this is used at 0.1% loading in an aliquot of absorbable gel former [Corbett, J. T. et al., In Vitro and In Vivo Release of Vancomycin and Gentamicin from an Injectable Absorbable Gel-forming Matrix for Treating Osteomyelitis, *Mater. Res. Soc.*, 351 (1997)] that is spread and allowed to gel (in the presence of water) on one side of the fabric on the same area as that of the treated fabric; (4) vancomycin as a positive control antibacterial agent for the *S. epidermidis* cultures-this is used at 0.1% loading in an aliquot of absorbable gel former [Corbett, J. T. et al, In Vitro and In Vivo Release of Vancomycin and Gentamicin From an Injectable Absorbable Gel-forming Matrix for Treating Osteomyelitis, *Mater. Res. Soc.*, 351 (1997)] in the manner as described in "3"; and (5) a set of 6–10 experiments for each type of fabric.

Based on the aforementioned strategy, the antibacterial activity of the fabrics is evaluated using, first, a qualitative procedure that is followed by a quantitative one. The qualitative procedure used is AATCC Test Method 147-1993 for antibacterial activity assessment of textile materials and is referred to as the Parallel Streak Method. This method is designed as a relatively quick and easily executed procedure to determine antibacterial activity of diffusable (or leachable) antimicrobial agents on treated textile materials. On the other hand, AATCC Test Method 100-1993 is also used as the quantitative procedure for the evaluation of the degree of antimicrobial activity of the treated fabrics. This procedure is adequately sensitive but cumbersome and time consuming for screening purposes. Therefore, as noted earlier, it is preceded by AATCC-Test Method 147-1993 for early evaluation of treated fabric samples. The effect of the washing cycle on the antibacterial activity of the fabric is used as an indicator of the controlled release of an antimicrobial agent.

It should be noted that the use of both methods allows for full assessment of the effectiveness of the treated fabrics with an extraordinary degree of confidence. In fact, if only bacteriostatic activity (inhibition of multiplication) is intended, a qualitative procedure, which clearly demonstrates antibacterial activity as contrasted with lack of such activity by an untreated specimen, may be acceptable. However, if bactericidal activity is intended, desired or implied, quantitative evaluation is necessary.

The foregoing description of preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

That which is claimed is:

1. An antimicrobial non-woven fabric comprising:
   a polymeric fiber substrate comprising phosphonic acid groups covalently bonded thereto and antimicrobial agents ionically bonded to the phosphonic acid groups.

2. An antimicrobial non-woven fabric as set forth in claim 1 wherein the polymeric fiber substrate comprises a polypropylene fiber substrate.

3. An antimicrobial non-woven fabric as set forth in claim 2 wherein the antimicrobial agents comprise benzalkonium chloride.

4. An antimicrobial non-woven fabric comprising:
   a polymeric fiber substrate comprising phosphonyl groups covalently bonded thereto, diamines bonded to the phosphonyl groups, and antimicrobial agents ionically bonded to the diamines.

5. An antimicrobial non-woven fabric as set forth in claim 4 wherein the polymeric fiber substrate comprises a polypropylene fiber substrate.

6. An antimicrobial non-woven fabric as set forth in claim 4 wherein the diamines comprise hexanediamine.

\* \* \* \* \*